(12) United States Patent
Faber et al.

(10) Patent No.: US 9,555,212 B2
(45) Date of Patent: Jan. 31, 2017

(54) ANESTHESIA SYSTEM WITH DETACHABLE ANESTHETIC DISPENSING DEVICE

(75) Inventors: Sönke Faber, Stockelsdorf (DE); Wolfgang Falb, Gross Sarau (DE); Michael Heidschmidt, Lübeck (DE); Sven Heyer, Lübeck (DE); Thomas Lutter, Lübeck (DE); Cornelia Marx, Lübeck (DE); Martin Meyer, Lübeck (DE); Sven Pasdzior, Lübeck (DE); Klaus Radomski, Lübeck (DE); Hartmut Stark, Stockelsdorf (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 1517 days.

(21) Appl. No.: 13/152,631

(22) Filed: Jun. 3, 2011

(65) Prior Publication Data
US 2011/0297148 A1 Dec. 8, 2011

(30) Foreign Application Priority Data

Jun. 5, 2010 (DE) .......................... 10 2010 022 828

(51) Int. Cl.
*A61M 16/01* (2006.01)
*A61M 16/18* (2006.01)

(52) U.S. Cl.
CPC ........ *A61M 16/186* (2013.01); *A61M 2205/18* (2013.01); *A61M 2205/3386* (2013.01);
(Continued)

(58) Field of Classification Search
CPC .............. A61M 16/0087; A61M 16/12; A61M 2202/0208; A61M 16/22; A61M 16/16; A61M 16/1075; A61M 16/18; A61M 2202/064; A61M 16/00; A61M 2016/0069; A61M 16/0808; A61M 16/186; A61M 2205/587; A61M 2205/3386; A61M 2205/3389; A61M 2205/584; A61M 2205/18; A61M 2205/6063; A61M 2205/502; A61B 18/14; A62B 23/02; A62B 23/025; A62B 19/00; A62B 7/10
(Continued)

(56) References Cited

U.S. PATENT DOCUMENTS 4,240,747 A 12/1980 Harmer
5,293,115 A * 3/1994 Swanson ........................ 324/110
(Continued)

FOREIGN PATENT DOCUMENTS

CN 101496925 A 8/2009
CN 201351874 Y 11/2009
(Continued)

OTHER PUBLICATIONS

German Examination Report of Sep. 29, 2014.

*Primary Examiner* — Peter Vasat
*Assistant Examiner* — Mark Wardas
(74) *Attorney, Agent, or Firm* — McGlew and Tuttle, P.C.

(57) ABSTRACT

An anesthesia system for providing a breathing gas enriched with anesthetic has an anesthesia apparatus (2) and at least one anesthetic dispensing device (3), which is detachably coupled with the anesthesia apparatus. A fluid connection (7, 8, 9) is provided between the anesthesia apparatus and the dispensing device, which is designed to send anesthetic from the dispensing device into the anesthesia apparatus. At least one optical interface is provided between the anesthesia apparatus and the dispensing device. At least one display device is provided in the dispensing device. The optical interface has at least one light source (10), which is provided in the anesthesia apparatus, and at least one fiber optic light guide (20), which is provided in the anesthetic dispensing device (3). The light fed by the light source (10) into the fiber optic light guide is sent to the display device to directly or indirectly light the display device.

20 Claims, 5 Drawing Sheets

(52) U.S. Cl.
CPC ......... *A61M 2205/3389* (2013.01); *A61M 2205/502* (2013.01); *A61M 2205/584* (2013.01); *A61M 2205/587* (2013.01); *A61M 2205/6063* (2013.01)

(58) Field of Classification Search
USPC .............. 128/203.16, 203.12, 203.14, 200.24,128/205.11, 205.27, 25.28, 204.18, 205.12
See application file for complete search history.

(56) References Cited

U.S. PATENT DOCUMENTS

| | | | |
|---|---|---|---|
| 5,293,865 | A | 3/1994 | Altner et al. |
| 6,422,073 | B1 | 7/2002 | Krahbichler et al. |
| 7,287,557 | B2 | 10/2007 | Bunke et al. |
| 7,621,677 | B2 * | 11/2009 | Yang et al. .............. 385/88 |
| 2002/0024654 | A1 * | 2/2002 | Park et al. ............. 356/73.1 |
| 2004/0021100 | A1 * | 2/2004 | Gouzman et al. ......... 250/573 |
| 2007/0097691 | A1 * | 5/2007 | Wu ...................... 362/293 |
| 2007/0287959 | A1 * | 12/2007 | Walter et al. ............ 604/131 |
| 2008/0236580 | A1 * | 10/2008 | Shang et al. ........... 128/203.16 |
| 2009/0194103 | A1 | 8/2009 | Thom et al. |
| 2011/0259334 | A1 * | 10/2011 | Alfieri et al. ........... 128/205.12 |

FOREIGN PATENT DOCUMENTS

| | | |
|---|---|---|
| DE | 694 766 C | 8/1940 |
| DE | 38 13 520 A1 | 11/1989 |
| DE | 10 2004 040 930 B3 | 9/2005 |
| DE | 102007014838 B3 | 3/2008 |
| EP | 1044700 A2 | 10/2000 |
| EP | 1961438 A1 | 8/2008 |

* cited by examiner

ANESTHESIA SYSTEM WITH DETACHABLE ANESTHETIC DISPENSING DEVICE

CROSS REFERENCE TO RELATED APPLICATIONS

This application claims the benefit of priority under 35 U.S.C. §119 of German Patent Application DE 10 2010 022 828.1 filed Jun. 5, 2010, the entire contents of which are incorporated herein by reference.

FIELD OF THE INVENTION

The present invention pertains generally to an anesthesia system for providing a breathing gas enriched with anesthetic. The present invention pertains, in particular, to an anesthesia system, which comprises an anesthesia apparatus and at least one anesthetic dispensing device, which is detachably coupled with the anesthesia apparatus. The anesthetic dispensing device contains essentially an anesthetic reservoir, in which anesthetic evaporates and a dispensing means to set the concentration of the anesthetic. The coupling between the at least one anesthetic dispensing device and the anesthesia apparatus proper is designed to bring about a fluid connection between the anesthesia apparatus and the at least one dispensing device, so that the gaseous anesthetic can be sent from the dispensing device into the anesthesia apparatus, where it is mixed at the set concentration with the breathing gas. Furthermore, contactless interfaces are provided, by means of which a contactless communication is made possible between the anesthesia apparatus and the at least one dispensing device. Finally, the dispensing device has at least one display means to display, for example, the set anesthetic concentration and the anesthetic filling level.

BACKGROUND OF THE INVENTION

Anesthesia systems are used, in general, to provide and dispense inhalation anesthetics for the purpose of anesthetizing patients, on which surgical procedures will be performed, in order to thus eliminate or reduce pain sensation. Mainly anesthetics in the vapor form are used in medical technology for anesthetizing patients during a surgical procedure. The prior-art anesthetic dispensing devices necessary for this and the anesthetic evaporators contained therein usually operate purely passively (with the exception of dispensing devices for desflurane), have no electronic interfaces and can be detachably or replaceably coupled with a corresponding anesthesia apparatus by means of standardized coupling devices.

In addition, electronic anesthesia systems are known, in which the anesthetic dispensing device is integrated in the anesthesia apparatus. The anesthetic dispensing device is monitored and controlled in these systems by the anesthesia apparatus itself, which has active, electronically controlled actuators as well as display means for the operating states. However, these systems have the drawback that the anesthetic dispensing device cannot be replaced in a simple manner when the anesthetic reserve has been used up. It is sometimes necessary in the course of anesthesia to replace the anesthetic. However, the dispensing device must be replaced with another dispensing device for this purpose. If a plurality of dispensing devices can be connected to the anesthesia apparatus, it is alternatively possible to change over from one dispensing device to the other. This can be achieved with the integrated systems at a great technical effort only at best.

While the patient data and relevant set parameters are displayed in the medical devices commonly used in the field of surgery usually either on luminescent displays or by means of optically active components (e.g., LEDs, seven-segment displays, etc.), such display means have not been known so far in connection with anesthetic dispensing devices. The parameters important for the monitoring and control of anesthesia, for example, anesthetic filling level and anesthetic concentration, can therefore be read only uncomfortably at best in the operating room or in a darkened environment in case of prior-art dispensing devices. Moreover, states of alarm are usually displayed on a central screen only. Direct assignment of the alarm to the component that causes the disturbance is not given or is insufficient.

In addition, other, essentially passively operating devices or device parts are in use, which lack a suitable electronic connection to a controlling device in order to make it possible, for example, to display alarm situations on site. This applies, for example, to pulmotors, flexible tube connections, syringe actuators, means for drop infusion, etc. In case of error, it would be helpful for the hospital staff to have the cause of error visualized directly at the site of the error in this case as well.

DE 38 13 520 A1 pertains generally to coding methods and coding devices for an anesthesia means as well as to the automatic recognition of an anesthetic evaporator and of the anesthetic being used. The anesthesia means contains the anesthesia apparatus proper and an anesthetic evaporator with a corresponding setting device. The anesthesia apparatus is provided with three reflective photoelectric cells, which are designed to send light signals, which are reflected by corresponding reflective marks (depending on the color thereof), which are arranged at an anesthetic evaporator coupled with the anesthesia apparatus. The light signals reflected by the reflective marks are detected by the reflective photoelectric cells, and the corresponding electric signals are sent to a measuring and monitoring unit for analysis. The type of anesthetic evaporator can be detected in this manner. Another recorder in the form of three strips arranged one above the other, on which a coding each, marked by white and black fields, is applied, is provided on the setting device designed as a handwheel for recognizing the anesthetic concentration set. The coding of the strips is entered by a scanning device by irradiating the strips with light beams through photoelectric cells in the anesthesia apparatus. The light beams are reflected when falling on a white surface and absorbed when falling on a black surface. The resulting electric signals are sent via a signal line to the same measuring and monitoring unit.

DE 10 2007 014 838 B3 describes an anesthesia system, which has an anesthesia apparatus, an anesthetic dispenser with an anesthetic reservoir, a dispensing parameter detection means and a contactless interface between the anesthesia apparatus and the anesthetic dispenser. The transmission of data (for example, anesthetic filling level) from the anesthetic dispenser to the anesthesia apparatus as well as the transmission of energy from the anesthesia apparatus to the anesthetic dispenser take place by means of electromagnetic fields. The measurement of the anesthetic filling level is performed by means of a glass tube, which is coupled with the anesthetic reservoir and is provided with capacitor surfaces, the anesthetic acting as a dielectric and a change in the anesthetic filling level in the glass tube leading to a corresponding change in capacity. The anesthetic concentration is set by means of a setting wheel on the anesthetic dispenser. The setting angle of the setting wheel is detected by means of an angle detection means, which is designed as an optical encoder.

Measures or means for visually displaying, for example, the position of the setting wheel for setting the concentration or the anesthetic filling level directly at the anesthetic dispensing device for being recognized by human operators (for example, the anesthesiologist) quickly and reliably even under poor lighting conditions, are not disclosed either in DE 38 13 520 A1 or DE 10 2007 014 838 B3.

The embodiments proposed in the state of the art make possible only an optoelectronic detection of various parameters, such as the filling level and anesthetic concentration, an anesthetic dispensing device and a corresponding anesthetic evaporator. Visual detection of these parameters directly at the dispensing device by human operators is hardly possible or requires increased attention, which is not always given uniformly due to stress during, for example, a longer-lasting anesthesia.

SUMMARY OF THE INVENTION

A basic object of the present invention is therefore to make available an anesthesia system with an anesthesia apparatus and with at least one replaceable anesthetic dispensing device, which system is designed to improve the visual display of various measured and set parameters of the anesthetic dispensing device or of the anesthetic storage reservoir contained in the dispensing device. The object of the present invention is, in particular, to display the setting of the anesthetic concentration and the anesthetic reserve in the at least one dispensing device such that recognizability is easily guaranteed, for example, even in a darkened environment even from a distance of 1-2 m. In addition, optical signals (e.g., alarms) shall be able to be generated in the dispensing device to make it possible, for example, to directly assign the alarm to the cause of the alarm (e.g., an empty storage reservoir or an anesthetic concentration set incorrectly). Furthermore, a solution that is cost-effective and operates in a contactless manner shall be obtained by means of the present invention. Finally, an independent, separate power supply shall be avoided in the anesthetic dispensing device.

The anesthesia system according to the present invention contains essentially an anesthesia apparatus, at least one anesthetic dispensing device with an anesthetic storage reservoir integrated therein as well as a contactless interface between the anesthesia apparatus and the anesthetic dispensing device. The interface of the anesthesia system preferably operates purely optically by means of fiber optic light guides, into which light is fed by a light source (for example, one or more LEDs). The light source including the necessary power supply is located in the anesthesia apparatus and is coupled with the anesthetic dispensing device via an optical interface. In the dispensing device or in the storage reservoir, the light fed into the at least one fiber optic light guide is sent via the fiber optic light guide(s) to at least one display means, for example, a sight glass or glass tube for displaying the anesthetic filling level and/or a setting wheel (rotating wheel) for setting the anesthetic concentration. The light emitted by the LEDs in the anesthesia apparatus, which light is sent via the optical interface and the at least one fiber optic light guide in the dispensing device to the at least one display means, can be used in this manner to directly or indirectly light the corresponding display means.

The at least one fiber optic light guide provided in the anesthetic dispensing device is either at least one glass/plastic fiber bundle (which, though flexible, is difficult to install) or at least one massive plastic fiber optic light guide (e.g., one made of Poly(methyl methacrylate) (PMMA)). The at least one massive plastic fiber optic light guide is preferred in terms of simple installation, because a fiber optic light guide manufactured according to the injection molding process can be adapted to the outer contour of the dispensing device or of the storage reservoir. However, this plastic fiber optic light guide must be designed carefully to guide the light without losses to the extent possible. An embodiment with two or more separate fiber optic light guides has the advantage that two or more objects (display means) in the dispensing device can be lit independently from one another.

In addition, an excessively low anesthetic filling level can be displayed by blinking and/or by variations of the color of the light at the sight glass/glass tube. For example, a normal filling level can be displayed by a constant green or blue light color, whereas an excessively low filling level is displayed by a blinking red light. This has the advantage for the anesthesiologist that he can localize the cause of the disturbances more quickly and respond to it immediately. A blinking red lighting of the setting wheel for setting the anesthetic concentration could indicate, for example, an erroneously opened storage reservoir or an excessively high concentration setting. It is possible, furthermore, due to the possibility of selecting different light colors (green, blue, yellow, red), to generate graduated warning messages in terms of urgency.

As was explained above, it is possible to use, for example, one or more LEDs as the light source. There also are multicolored LEDs, which comprise a plurality of individual chips. LEDs are, in general, to be preferred to incandescent lamps because of their long service life and the better possibility of actuation. In addition, the light emitted by the LEDs can be better coupled into a fiber optic light guide.

The optical interface between the anesthesia apparatus and the dispensing device contains at least one fiber optic light guide, which is mounted in the dispensing device, and at least one LED, which is mounted in the anesthesia apparatus such that the light exit area of the at least one LED is located at a side wall of the anesthesia apparatus, namely, at the site at which the dispensing device is coupled with the anesthesia apparatus. If the dispensing device is arranged at the anesthesia apparatus (i.e., it is coupled detachably), the light exit area of the at least one LED is consequently located at the side wall of the anesthesia apparatus directly opposite and aligned with the light exit area of the at least one fiber optic light guide in the dispensing device, namely, at a short distance of about 0.5 mm to 10 mm. The light emitted by the at least one LED is thus fed from the light exit area of the at least one LED through the air gap between the anesthesia apparatus and the dispensing device into the light exit area of the at least one fiber optic light guide. The light is sent through the at least one fiber optic light guide to the light exit area thereof and radiated through this to the respective object (display means) to be lit in the dispensing device.

It is possible now for an individual LED to feed the fiber optic light guide/fiber optic light guides for lighting the sight glass or glass tube and for lighting the setting wheel together. As an alternative, it is also possible to provide a transmitting unit with two LEDs in order to supply two corresponding fiber optic light guides with light individually. It is, of course, possible to use more than two LEDs in combination with a corresponding number of fiber optic light guides.

To compensate tolerances of the suspension or coupling of the at least one dispensing device on or with the anesthesia apparatus, which tolerances may lead to a certain axial offset (<2 mm) between the light exit area of the LED(s) and the light exit area of the corresponding fiber optic light guide, it may be possibly necessary to correct these tolerances by an automatic readjustment during the coupling of the dispensing device with the anesthesia apparatus. For example, a mechanical lever mechanism or a similar mechanical adjusting means may be used for this, in which case either the suspension of the fiber optic light guide in the dispensing device is adjusted in height or the holder of the LED in the anesthesia apparatus is brought to the same level as the fiber optic light guide/fiber optic light guides. The light exit area of the at least one LED can be brought in this manner into correct alignment with the light exit area of the corresponding fiber optic light guide. Further solutions will be explained below.

The present invention will be described now on the basis of some exemplary embodiments with reference to the figures, on the basis of which various embodiments of the anesthesia system according to the present invention will be explained. However, the present invention is not limited to these exemplary embodiments. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
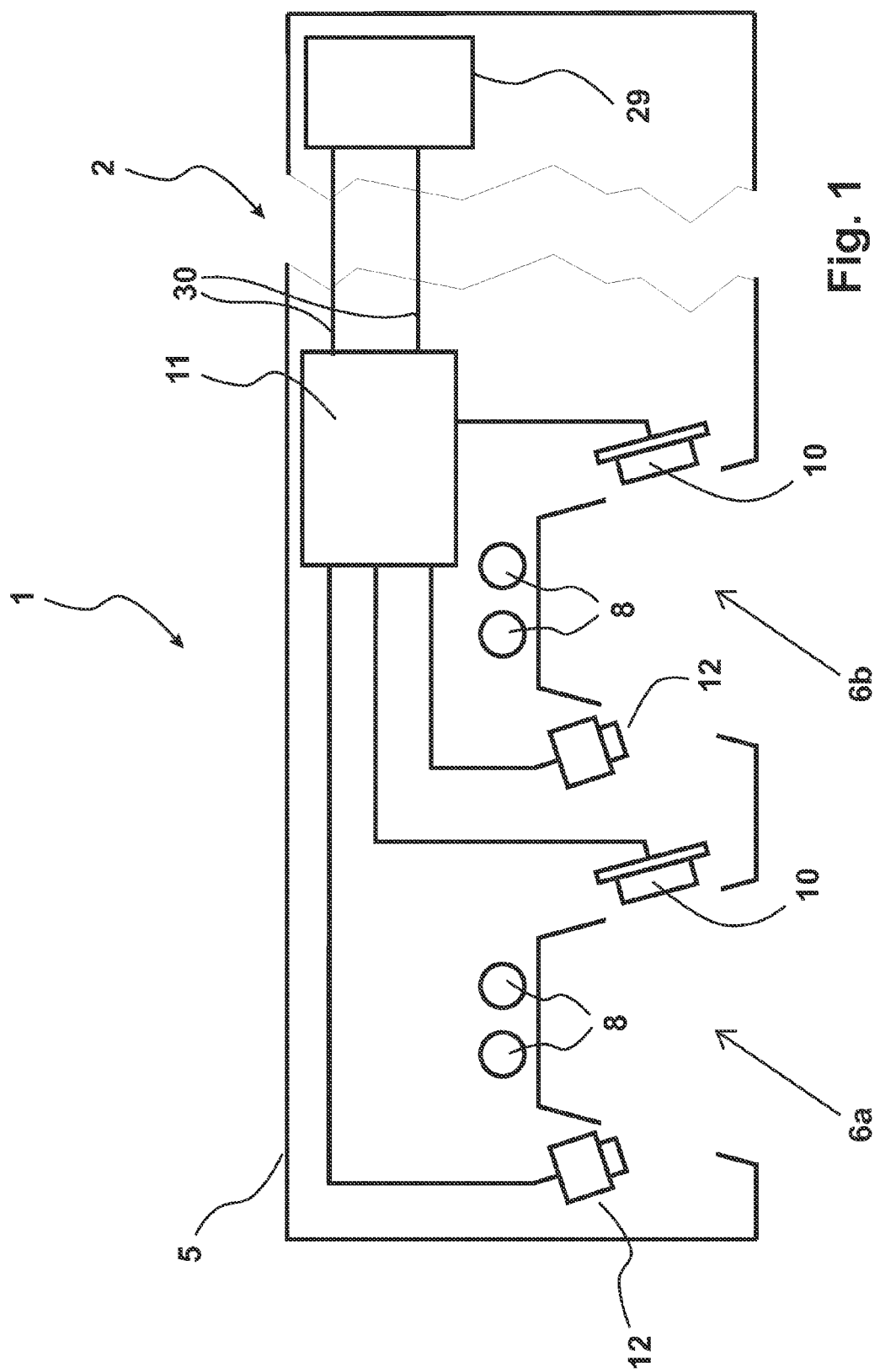
FIG. 1 is a schematic top sectional view of an exemplary mounting arm of an anesthesia apparatus, which is designed to mount two anesthetic dispensing devices.
Figure 2:
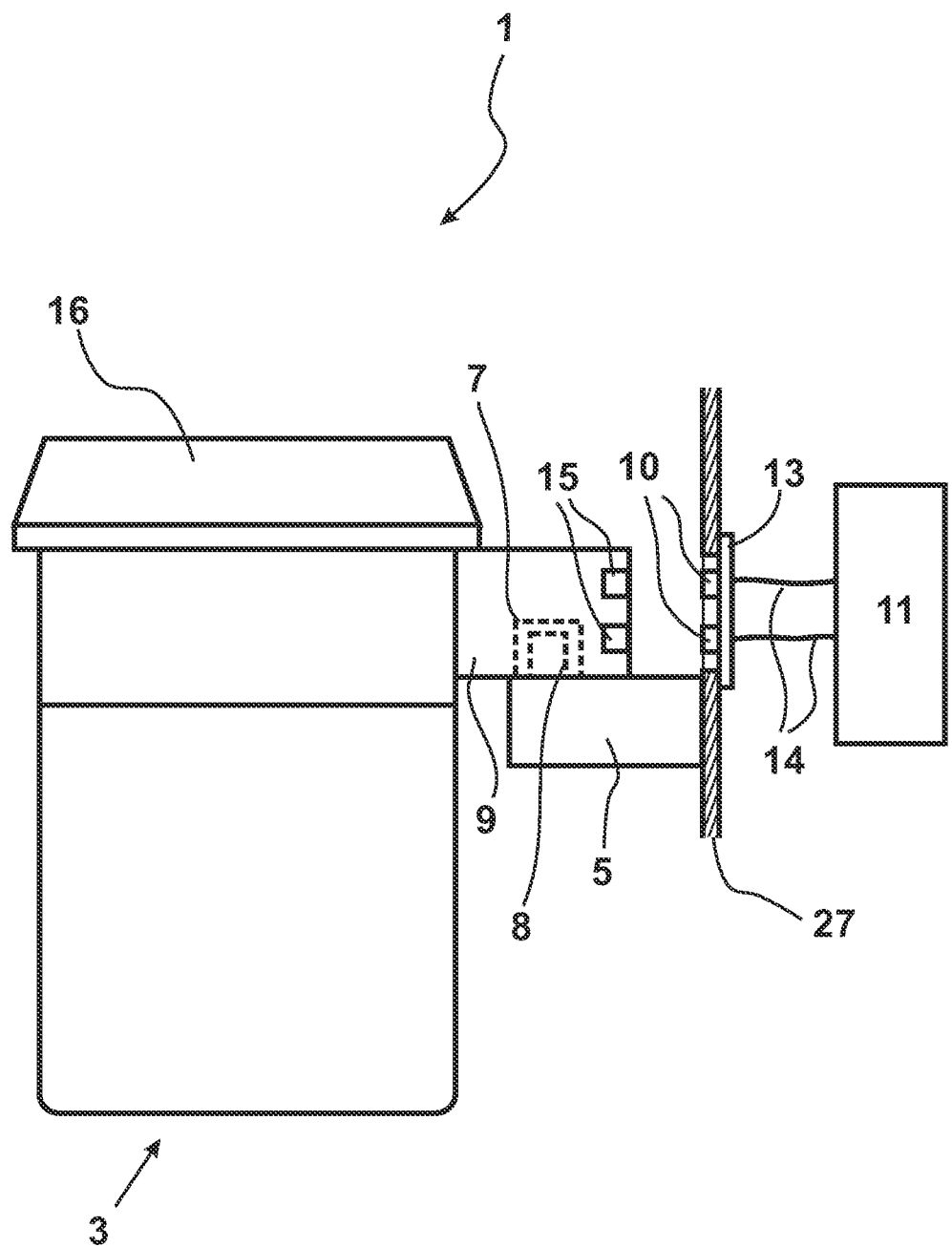
FIG. 2 is a partially sectional side view of an anesthetic dispensing device, which is arranged on the mounting arm from FIG. 1.

Referring to the drawings in particular, as was explained above, the anesthesia system 1 according to the present invention, which can be seen in FIGS. 1 and 2, comprises an anesthesia apparatus 2 and at least one anesthetic dispensing device 3, which is detachably coupled with the anesthesia apparatus 2 and which contains an anesthetic storage reservoir 4, in which anesthetic evaporates. The anesthesia apparatus 2 is provided with at least one mounting arm 5, which is shown in a cross-sectional view in the top part of FIG. 1. The exemplary mounting arm 5 is provided with two recesses 6a, 6b, which are designed to receive two dispensing devices 3. Mounting arm 5 is provided for this purpose with two holding pins 8 at each of the recesses 6a, 6b, which said holding pins 8 are used for being received in corresponding holes 7, which are formed in a bracket 9 of the dispensing device (shown in FIG. 2). The basic principle of this structure forms a fluid connection 7, 8 between the anesthesia apparatus 2 and the anesthetic dispensing device 3. The basic principle of this mounting structure is schematically shown in FIG. 2, and it is obvious to the person skilled in the art that the holding pins 8 are of a tubular design and that by the holding pins 8 engaging the holes 7, the fluid connection is established between the dispensing device 3 and the anesthesia apparatus 2 in order to deliver anesthetic at a set concentration from the dispensing device 1 to the anesthesia apparatus 2. It is, of course, also possible, in principle, to form the holes 7 in the anesthesia apparatus and the holding pins 8 in the dispensing device As is also shown in FIG. 1, the mounting arm 5 has one or more light sources 10 on an outer wall of the recesses 6a, 6b. The light sources 10 are preferably formed by one or more LEDs. At least one LED is positioned such that its light exit area is directed into the recess, so that the light of the at least one LED is emitted essentially at right angles to the wall of the recess. The LEDs in the two recesses 6a, 6b are supplied by a control unit 11, which is connected with a serial interface RS 232 (or with another serial/parallel interface) 30 and a power supply unit $U_{Vers}$ 29.

If the dispensing devices 3 are coupled with the mounting arm 5 of the anesthesia apparatus 2 by means of the holding pins 8 and holes 7, the light exit areas of the LEDs 10 are aligned with the corresponding light exit areas of the fiber optic light guides in the respective dispensing device. Adjusting means are preferably provided in order to make it possible to correct possible deviations.

Finally, FIG. 1 shows optical detectors 12, which are represented as cameras. The optical detectors 12 are designed and arranged to optically detect, for example, the display means (e.g., filling level and concentration setting) of the respective dispensing device. For example, the anesthetic filling level or anesthetic concentration set can be detected in this manner optoelectronically. The measured signals are sent to the control unit, so that the measured values of the filling level and concentration can be displayed, for example, on an external monitor. In addition, the measured values can be compared with limit values, and a corresponding alarm message is sent if the measured values drop below or exceed these limit values. This message may be acoustic, but such alarm messages are preferably generated optically by emitting different light colors. In other words, the at least one LED emits light in different colors, depending on the operating state or the state of alarm, so that the corresponding display means are lit with the corresponding light color. Furthermore, it is possible to generate an alarm by blinking light.

FIG. 2 shows a mounting arm 5 of the anesthesia apparatus 2 together with a coupled dispensing device 3 as a schematic side view in such a way that it can be easily distinguished from the view in FIG. 1 in order to make it possible to show the optical interface between the anesthesia apparatus 2 and the dispensing device better. Two LEDs 10 are arranged at a wall of the mounting arm 5. The dispensing device is shown for this purpose offset to the left relative to the mounting arm 5. This also causes the holding pin 8 indicated by broken lines to have likewise been shown offset to the left compared to its actual position on the mounting bracket 5.

The two LEDs 10 are arranged at a wall 27 of the mounting arm 5. The LEDs 10 are arranged on a board 13, which is fastened to an inner wall of the mounting arm 5. The LEDs are connected to the control unit 11 via control lines 14. For example, holes are formed in the wall 27 of mounting arm 5, and these holes are essentially aligned with the light exit areas of the LEDs 10, so that the LEDs emit light through these holes in a direction essentially at right angles to the wall surface 27 of mounting arm 5. As is also shown in FIG. 2, light entry areas 15, which are embodied preferably by correspondingly designed ends of fiber optic light guides 20 (FIGS. 4, 5, 6, 7 and 8), which are arranged in the dispensing device 3, are provided in bracket 9 of the dispensing device 3. These fiber optic light guides, which are not shown in FIG. 2 for the sake of clarity, extend from the light entry areas 15 through the bracket 9 into the housing of the dispensing device 3. The ends (light exit areas) of the fiber optic light guides are preferably located in the vicinity of the display means to be lit, i.e., in the vicinity of the setting wheel 16 of the dispensing device for setting the anesthetic concentration and in the vicinity of a sight glass (glass tube) for displaying the anesthetic filling level. The setting wheel and the glass tube are lit in this manner, so that reading is guaranteed even under unfavorable light conditions. As was explained above, the LED or LEDs is/are preferably able to emit light in different colors. The glass tube and setting wheel can thus be radiated, for example, with green or blue light when the filling level or set concentration is within the desired range. Should the concentration be set incorrectly or should the filling level be too low, the rotating wheel or glass tube is radiated, for example, with red light. In addition, warning messages can be embodied by blinking light.

Figure 3:
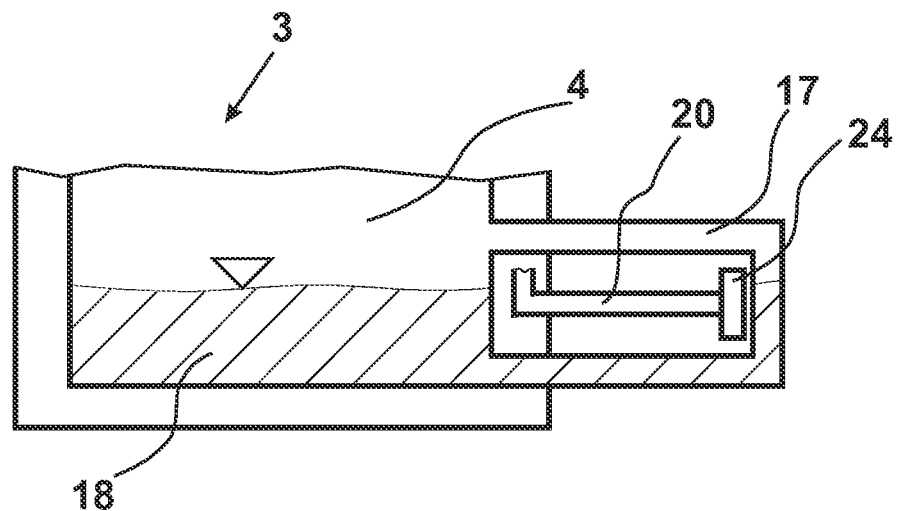
FIG. 3 is a cross-sectional view of the anesthetic dispensing device from FIG. 2 with a reservoir contained therein, which is provided with a measuring tube/sight glass.

FIG. 3 shows a side view in the cross section for a lower area of the anesthetic dispensing device 3 from FIG. 2 with the anesthetic reservoir 4 contained therein, which is connected to a measuring tube 17 (glass tube). As is apparent from FIG. 3, the filling level of the anesthetic 18 is displayed in the glass tube. The above-described fiber optic light guide 20 is arranged with its light exit area such that the light emitted from the light exit area falls on the glass tube. To achieve the most uniform lighting of the glass tube possible, the fiber optic light guide 20 ends in this exemplary embodiment in a planar fiber optic light guide, which is designed as a plate-like body 24 and will be described in more detail below on the basis of FIG. 7.

Figure 4:
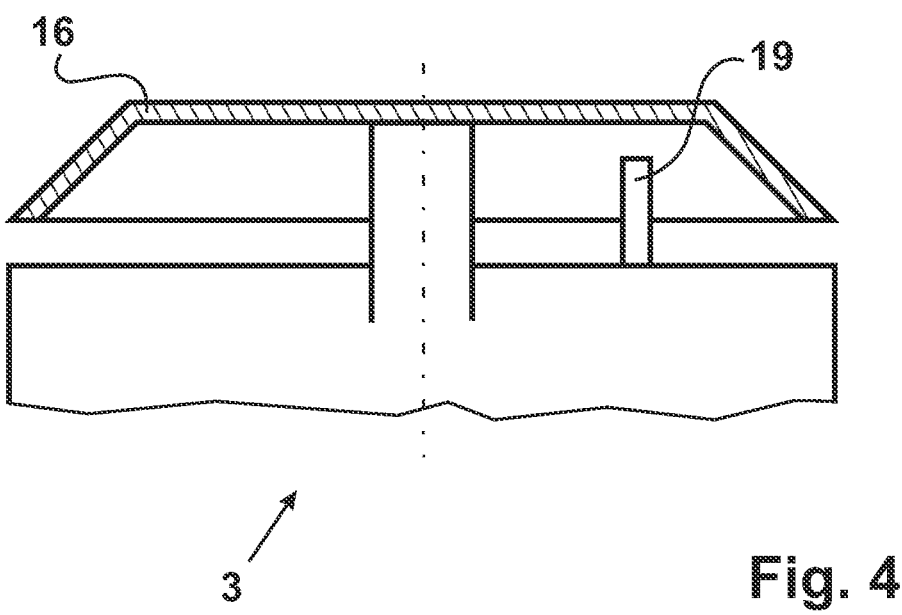
FIG. 4 is a cross-sectional view of a setting wheel/rotating wheel for setting the anesthetic concentration.

FIG. 4 shows a side view in the cross section for a setting wheel 16 for setting the anesthetic concentration, which wheel 6 is provided on the top side of the anesthetic evaporator 4 of the dispensing device 3. The setting wheel is transparent to light in the exemplary embodiment being shown. FIG. 4 shows, moreover, the end area 19 of a fiber optic light guide 20, whose light exit area radiates towards the inside of the setting wheel, so that the setting of the setting wheel can be easily recognized even under unfavorable lighting conditions.

Figure 5:
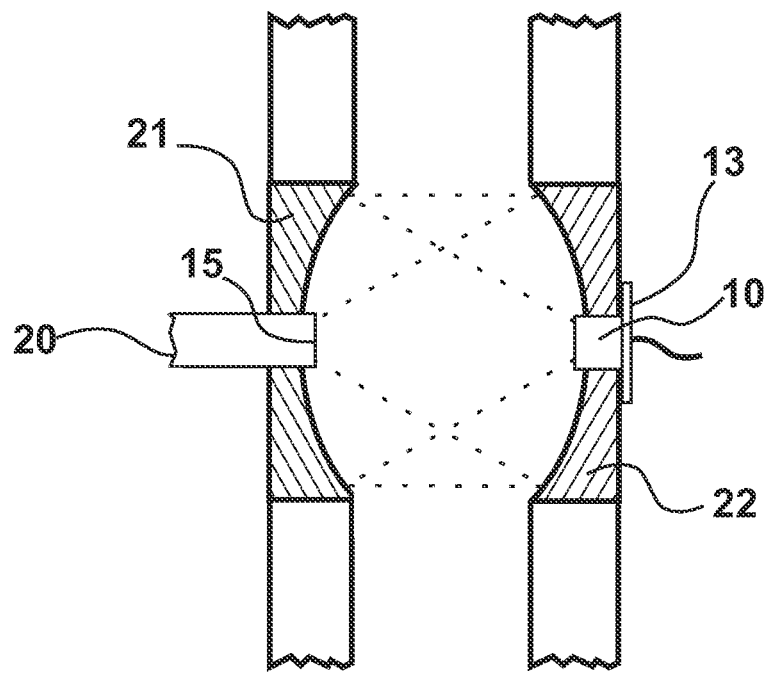
FIG. 5 is a schematic side view of the optical interface between the anesthesia apparatus and the dispensing device.
Figure 6:
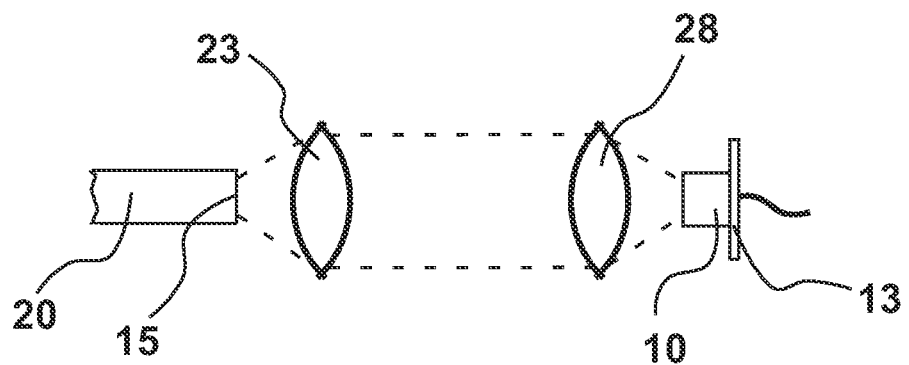
FIG. 6 is a schematic side view of an alternative embodiment of the optical interface between the anesthesia apparatus and the dispensing device.
Figure 7:
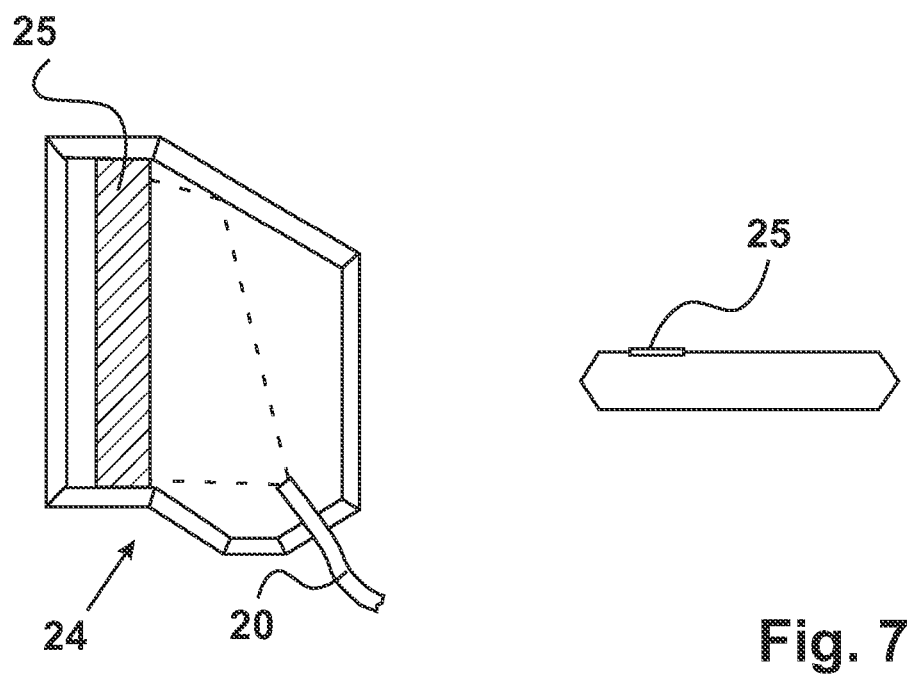
FIG. 7 is a side view of a planar fiber optic light guide used to make possible the exit of light over a large area and diffusely.

FIG. 5 shows a schematic side view of a first exemplary embodiment of the optical interface between the anesthesia apparatus 2 and dispensing device 3, and FIG. 6 is a schematic side view of a second, alternative embodiment of this optical interface. As was explained in the introduction, there are certain tolerances concerning the coupling of the dispensing device with the anesthesia apparatus 2, which may possibly have to be compensated in order to guarantee the optimal feed of the light emitted by the LED (or LEDs) into the fiber optic light guide (fiber optic light guides). These tolerances can be corrected by means of mechanical adjusting devices. As an alternative, the light entry area 15 of the fiber optic light guide 20 is irradiated by the opposite LED 10 such that the fiber optic light guides are always lit uniformly in case of deviations within the tolerance range. However, an additional luminous power of the LED is necessary in this case (this would be 224% in case of a fiber optic light guide diameter of e.g., 5 mm and tolerances of +/−2 mm and this corresponds to an additional luminous power of 96% at a tolerance of +/−1 mm). In addition, this scattered light would have to be absorbed in a suitable manner in order not to reach the surrounding area in an interfering manner. The coupling site (i.e., the light entry area 15) of the fiber optic light guide 20 is provided for this purpose, for example, with a collar 21 made of a black plastic, which predominantly absorbs light and reflects the residual part onto the LED side, where a collar 22 of the same type absorbs additional parts (FIG. 5). As an alternative, the outer surfaces of the collars 21, 22 may also be provided with a light-reflecting coating in order to reflect the scattered light at least partly onto the light entry area of the fiber optic light guide 20.

In the second embodiment (see FIG. 6), the luminous power of LED 10 is expanded with a lens 28 to a larger beam cross section with parallel ray path in this case (collimator) in order to subsequently focus this light by another lens 23 arranged in front of the light entry area 15 of the fiber optic light guide 20 into this light entry area. The interface is located here in the expanded part of the ray path, and an offset due to tolerance has a weaker effect in terms of percentage on the coupled light intensity.

To light the glass tube 17 shown in FIG. 3 for displaying the anesthetic filling level, it is necessary to allow the light intensity being carried by the fiber optic light guide 20 to exit as uniformly as possible behind or next to the glass tube 17. For example, planar fiber optic light guides may be used for this (see FIG. 7), which consist essentially of a plate-like body 24 made of an optically transparent material (glass, plastic). If the fiber optic light guide 20 is inserted into this body 24, the light can be distributed uniformly by total reflection on the lateral surfaces in the interior of the body 24 and it can exit the body at defined sites. This can be achieved either by the essentially mirror-finished body being roughened in an area 25, so that the light is scattered and uncoupled diffusely, or by the body being coated with a highly reflective material with the exception of the entry and exit sites. As an alternative to this, a plurality of fiber optic light guides 20 may be provided as well.

Figure 8:
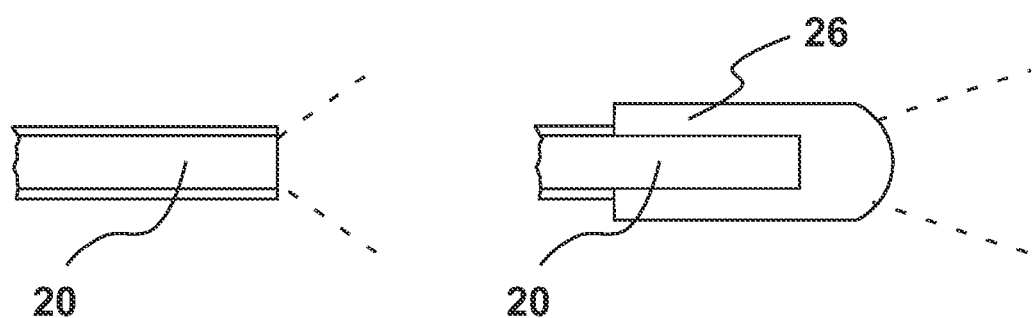
FIG. 8 is a lens attachment, which is arranged at the end of a fiber optic light guide in order to bring about focusing of the light exiting from the fiber optic light guide.

Since it is not necessary during the lighting of the setting wheel to light the entire rotating wheel (see FIG. 4), it is meaningful to limit the available light intensity to the area around the setting mark only. This can be advantageously achieved by means of a lens attachment 26 at the end of the fiber optic light guide 20 (FIG. 8). The view on the left side of FIG. 8 shows the fiber optic light guide 20 without lens attachment, whereas the view on the right side of FIG. 8 shows the fiber optic light guide with the lens attachment 26. The lighting intensity can be markedly increased in the range of interest by such a lens attachment 26 by the light emitted from the light exit area of the fiber optic light guide being focused.

Appendix

| LIST OF REFERENCE NUMBERS | |
|---|---|
| 1 | Anesthesia system |
| 2 | Anesthesia apparatus |
| 3 | Anesthetic dispensing device |
| 4 | Anesthetic storage reservoir |
| 5 | Mounting arm |
| 6a, 6b | Recesses |
| 7 | Holes |
| 8 | Holding pin |
| 9 | Brackets of the dispensing device |
| 10 | Light sources |
| 11 | Control unit |
| 12 | Optical detectors |
| 13 | Board |
| 14 | Control line |
| 15 | Light entry openings |
| 16 | Rotating wheel |
| 17 | Glass tube |
| 18 | Anesthetic |
| 19 | End area of fiber optic light guide |
| 20 | Fiber optic light guide |
| 21, 22 | Collar |
| 23 | Lens |
| 24 | Body |
| 25 | Roughened area |
| 26 | Lens attachment |
| 27 | Wall |
| 28 | Lens |
| 29 | Power supply |
| 30 | Interface |

What is claimed is:

1. An anesthesia system for providing breathing gas enriched with anesthetic, the anesthesia system comprising:
an anesthesia apparatus;
an anesthetic dispensing device detachably coupled with the anesthesia apparatus;
a fluid connection between the anesthesia apparatus and the anesthetic dispensing device, to send anesthetic from the anesthetic dispensing device into the anesthesia apparatus;
an optical interface between the anesthesia apparatus and the dispensing device; and
a display device connected to the anesthetic dispensing device, wherein the optical interface has a light source connected to the anesthesia apparatus, and a fiber optic light guide is provided connected to the anesthetic dispensing device and wherein the light fed by the light source into the fiber optic light guide is sent via the fiber optic light guide to the display device to directly or indirectly light the display device to provide a visual indication of at least one of filling level and concentration setting.

2. An anesthesia system in accordance with claim 1, wherein the light source is formed by one or more LEDs.

3. An anesthesia system in accordance with claim 1, wherein the light source and an energy supply unit therefor are located in the anesthesia apparatus.

4. An anesthesia system in accordance with claim 1, wherein the display device comprises an anesthetic filling level display for the display of an anesthetic filling level and a setting wheel for setting an anesthetic concentration.

5. An anesthesia system in accordance with claim 1, wherein the fiber optic light guide is provided in the anesthetic dispensing device and comprises a glass/plastic fiber bundle or a massive plastic fiber optic light guide.

6. An anesthesia system in accordance with claim 1, wherein the light source is formed by one or more LEDs, which emit light with different colors.

7. An anesthesia system in accordance with claim 1, wherein:
the light source is provided, in the anesthesia apparatus, and the anesthesia apparatus includes a light exit area, of the light source, on an outer wall of the anesthesia apparatus; and
the fiber optic light guide is in the anesthetic dispensing device and the fiber optic light guide has a light entry area on an outer wall of the anesthetic dispensing device, which light entry area is located opposite the light source when the anesthetic dispensing device is coupled with the anesthesia apparatus.

8. An anesthesia system in accordance with claim 7, wherein the light exit area of the light source in the anesthesia apparatus is arranged at a short distance from about 0.5 mm to 10 mm directly opposite to and aligned with the light entry area of the fiber optic light guide in the dispensing device.

9. An anesthesia system in accordance with claim 1, wherein light emitted by the light source is fed from a light exit area of the light source through an air gap between the anesthesia apparatus and the anesthetic dispensing device into a light entry area of the fiber optic light guide.

10. An anesthesia system in accordance with claim 1, wherein the anesthesia apparatus is provided with a mounting location for each said anesthetic dispensing device, with at least two holding pins, which are used for being received in corresponding holes provided at each anesthetic dispensing device.

11. An anesthesia system in accordance with claim 10, wherein meshing of the holding pins with the corresponding holes leads to an establishment of the fluid connection between the dispensing device and the anesthesia apparatus to deliver anesthetic from the dispensing device to the anesthesia apparatus.

12. An anesthesia system or providing breathing gas enriched with anesthetic, the anesthesia system comprising:
an anesthesia apparatus;
an anesthetic dispensing device detachably coupled with the anesthesia apparatus;
a fluid connection between the anesthesia apparatus and the anesthetic dispensing device, to send anesthetic from the anesthetic dispensing device into the anesthesia apparatus;
an optical interface between the anesthesia apparatus and the dispensing device; and
a display device connected to the anesthetic dispensing device, wherein the optical interface has a light source connected to the anesthesia apparatus, and a fiber optic light guide is provided connected to the anesthetic dispensing device and wherein the light fed by the light source into the fiber optic light guide is sent via the fiber optic light guide to the display device to directly or indirectly light the display device, wherein:
the light source is provided, in the anesthesia apparatus, and the anesthesia apparatus includes a light exit area, of the light source, on an outer wall of the anesthesia apparatus;
the fiber optic light guide is in the anesthetic dispensing device and the fiber optic light guide has a light entry area on an outer wall of the anesthetic dispensing device, which light entry area is located opposite the light source when the anesthetic dispensing device is coupled with the anesthesia apparatus; and the light exit area of the light source and the light entry area of the fiber optic light guide is provided with a collar made of a material that predominantly absorbs light, so that light radiating from the light source is partly absorbed by the collar at the light entry area and a remaining part of the radiating light is reflected onto the collar of the light exit area, where a portion of the reflected light is absorbed another portion of the reflected light is reflected into the light entry area.

13. An anesthesia system in accordance with claim 1, further comprising:

a lens; and another lens, wherein the light emitted by the light source is expanded by the lens to a larger beam cross section with an essentially parallel ray path, which is then focused by another lens in front of the light entry area of the fiber optic light guide into a light entry area.

14. An anesthesia system for providing breathing gas enriched with anesthetic, the anesthesia system comprising:

an anesthesia apparatus with an anesthetic dispensing device mounting site;

an anesthetic dispensing device detachably coupled with the anesthesia apparatus at the anesthetic dispensing device mounting site;

a fluid connection between the anesthesia apparatus at the anesthetic dispensing device mounting site and the anesthetic dispensing device, to send anesthetic from at least one said anesthetic dispensing device into the anesthesia apparatus;

a display device connected to the anesthetic dispensing device;

an optical interface between the anesthesia apparatus and the anesthetic dispensing device at the anesthetic dispensing device mounting site, the optical interface having a light source connected to the anesthesia apparatus and located at or adjacent to the anesthetic dispensing device mounting site and directed toward the anesthetic dispensing device at the anesthetic dispensing device mounting site and a fiber optic light guide associated with the anesthetic dispensing device, the optical interface directing light, fed by the light source into the fiber optic light guide, to the display device to directly or indirectly light the display device to provide a visual indication of at least one of filling level and concentration setting.

15. An anesthesia system in accordance with claim 14, wherein the light source is formed by one or more LEDs and the light source and an energy supply unit therefor are located in the anesthesia apparatus.

16. An anesthesia system in accordance with claim 14, further comprising:

an optical detector arrangement for detecting a display of the display device, wherein the display device comprises at least one of an anesthetic filling level display for the display of a anesthetic filling level and a setting wheel for the display of a setting of an anesthetic concentration.

17. An anesthesia system in accordance with claim 14, wherein the fiber optic light guide is provided in the anesthetic dispensing device and comprises a glass/plastic fiber bundle or a massive plastic fiber optic light guide.

18. An anesthesia system in accordance with claim 14, wherein:

the light source is provided in the anesthesia apparatus and the anesthesia apparatus includes a light exit area on an outer wall of the anesthesia apparatus;

the fiber optic light guide is in the anesthetic dispensing device and has a light entry area on an outer wall of the anesthetic dispensing device, which is located opposite the light source when the anesthetic dispensing device is coupled with the anesthesia apparatus; and the light exit area of the light source in the anesthesia apparatus is arranged at a short distance from about 0.5 mm to 10 mm directly opposite to and aligned with the light entry area of the fiber optic light guide in the anesthetic dispensing device.

19. An anesthesia system in accordance with claim 14, wherein the anesthesia apparatus is provided with a mounting location for each said anesthetic dispensing device with at least two holes, which are used to receive corresponding holding pins provided at each said anesthetic dispensing device, with the holes and pins forming part of the fluid connection, wherein an engagement of the holding pins with the corresponding holes leads to an establishment of the fluid connection between the anesthetic dispensing device and anesthesia apparatus to deliver anesthetic from the anesthetic dispensing device to the anesthesia apparatus.

20. An anesthesia system in accordance with claim 14, wherein the optical interface further comprises:

a lens; and another lens, wherein the light emitted by the light source is expanded by the lens to a larger beam cross section with an essentially parallel ray path, which is then focused by the another lens in front of the light entry area of the fiber optic light guide into a light entry area.

* * * * *